United States Patent
Jeannot et al.

(10) Patent No.: US 8,488,112 B2
(45) Date of Patent: Jul. 16, 2013

(54) METHOD FOR CONTACTLESS MEASUREMENT OF THE DENSITY OF A POROUS MATERIAL, USING A MEASUREMENT OF THE REFRACTIVE INDEX OF THE MATERIAL BY OPTICAL COHERENCE TOMOGRAPHY

(75) Inventors: Laurent Jeannot, Is sur Tille (FR); Florent Sandras, Martignas sur Jalle (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 172 days.

(21) Appl. No.: 13/057,153

(22) PCT Filed: Aug. 3, 2009

(86) PCT No.: PCT/EP2009/060021
§ 371 (c)(1),
(2), (4) Date: Feb. 1, 2011

(87) PCT Pub. No.: WO2010/015594
PCT Pub. Date: Feb. 11, 2010

(65) Prior Publication Data
US 2011/0134414 A1 Jun. 9, 2011

(30) Foreign Application Priority Data
Aug. 5, 2008 (FR) ................................. 08 55426

(51) Int. Cl.
*G01N 21/00* (2006.01)
*G01N 21/41* (2006.01)
*G01N 21/43* (2006.01)

(52) U.S. Cl.
USPC .............................................. 356/72; 356/517

(58) Field of Classification Search
USPC .......................... 356/72, 128, 129, 517, 518
See application file for complete search history.

(56) References Cited

U.S. PATENT DOCUMENTS

| | | | |
|---|---|---|---|
| 7,307,740 B2 | 12/2007 | Lamy et al. | |
| 7,864,339 B2 | 1/2011 | Jeannot et al. | |
| 2008/0074680 A1* | 3/2008 | Laurent et al. | 356/601 |

FOREIGN PATENT DOCUMENTS

| | | |
|---|---|---|
| WO | 2004083772 A2 | 9/2004 |
| WO | 2006030149 A1 | 3/2006 |
| WO | 2008023024 A1 | 2/2008 |

OTHER PUBLICATIONS

Almeida, R.M., "Sol-Gel Silica Films on Silicon Substrates," International Journal of Optoelectrics Incorporating Optical Computing and Processing, vol. 9, No. 2, Mar./Apr. 1994, pp. 135-142.

Veilleux, J. et al., "Optical Coherence Tomography for the Inspection of Plasma-Sprayed Ceramic Coatings," Journal of Thermal Spray Technology, vol. 16, No. 3, Sep. 2007, pp. 435-443.

(Continued)

*Primary Examiner* — Gregory J Toatley
*Assistant Examiner* — Dominic J Bologna
(74) *Attorney, Agent, or Firm* — Nixon Peabody LLP

(57) ABSTRACT

A method for contactless measurement of the density of a porous material, using a measurement of the refractive index of the material by optical coherence tomography.

Figure 3:
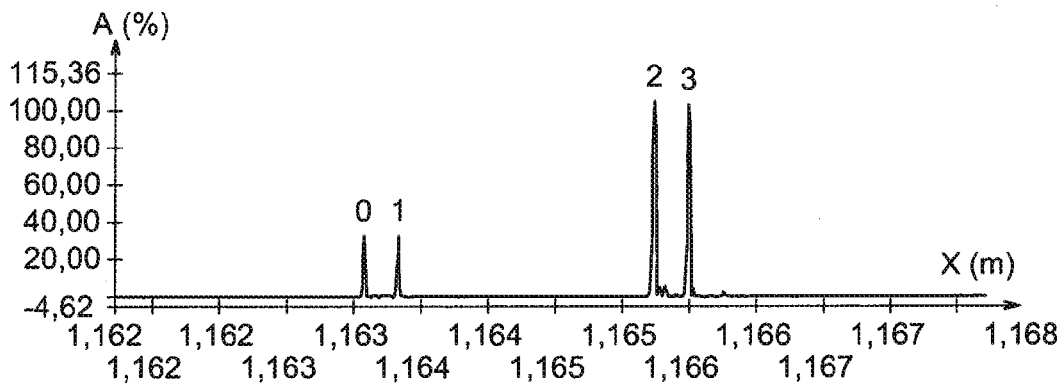

In the optical coherence tomography technique, the optical path corresponding to the crossing of an object made of the material by a light beam used in the technique, is determined, the thickness of the object is determined, the refractive index of the material is determined from the optical path and from the thickness, and the density of the material is determined from the refractive index.

3 Claims, 3 Drawing Sheets

OTHER PUBLICATIONS

Sorin, W. V. et al., "Simultaneous Thickness and Group Index Measurement Using Optical Low-Coherence Reflectometry," IEEE Photonics Technology Letters, vol. 4, No. 1, Jan. 1992, pp. 105-107.

Koresheva, E. R. et al., "Creation of a Diagnostic Complex for the Characterization of Cryogenic Laser-Fusion Targets Using the Tomography Method with Probing Irradiation in the Visible Spectrum," Journal of Russian Laser Research, vol. 28, No. 2, Mar. 2007, pp. 163-206.

Choux, A. et al., "Spatial Reconstruction Algorithm of DT Layer in Cryogenic Targets Using Optical Techniques," Fusion Science and Technology, vol. 51, No. 4, May 2007, pp. 727-736.

Veilleux, J. et al., "Particle Size Measurement in Glass Powder Beds Using Optical Coherence Tomography," Optical Engineering, vol. 47, No. 3, Mar. 2008, pp. 033601-1-033601-9.

International Search Report in International Application No. PCT/EP2009/060021, mailed Oct. 26, 2009.

International Preliminary Report on Patentability in International Application No. PCT/EP2009/060021, dated Oct. 14, 2010.

French Search Report in French Patent Application No. 0855426, dated Mar. 13, 2009.

* cited by examiner

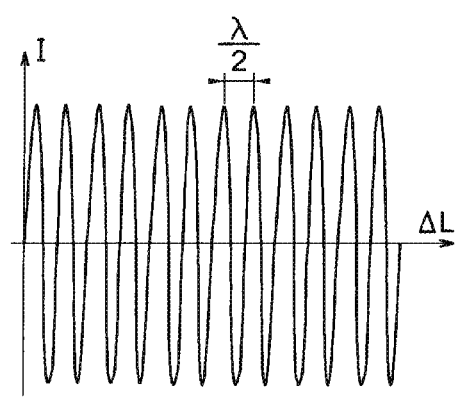
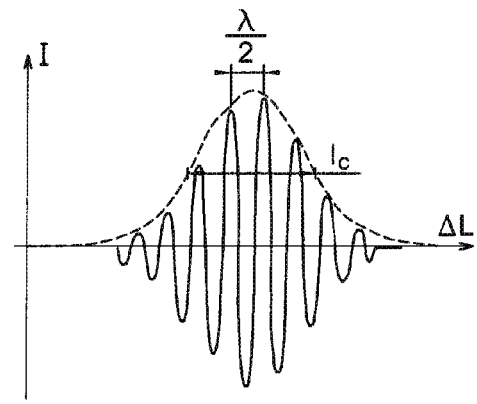
FIG. 1A  FIG. 1B
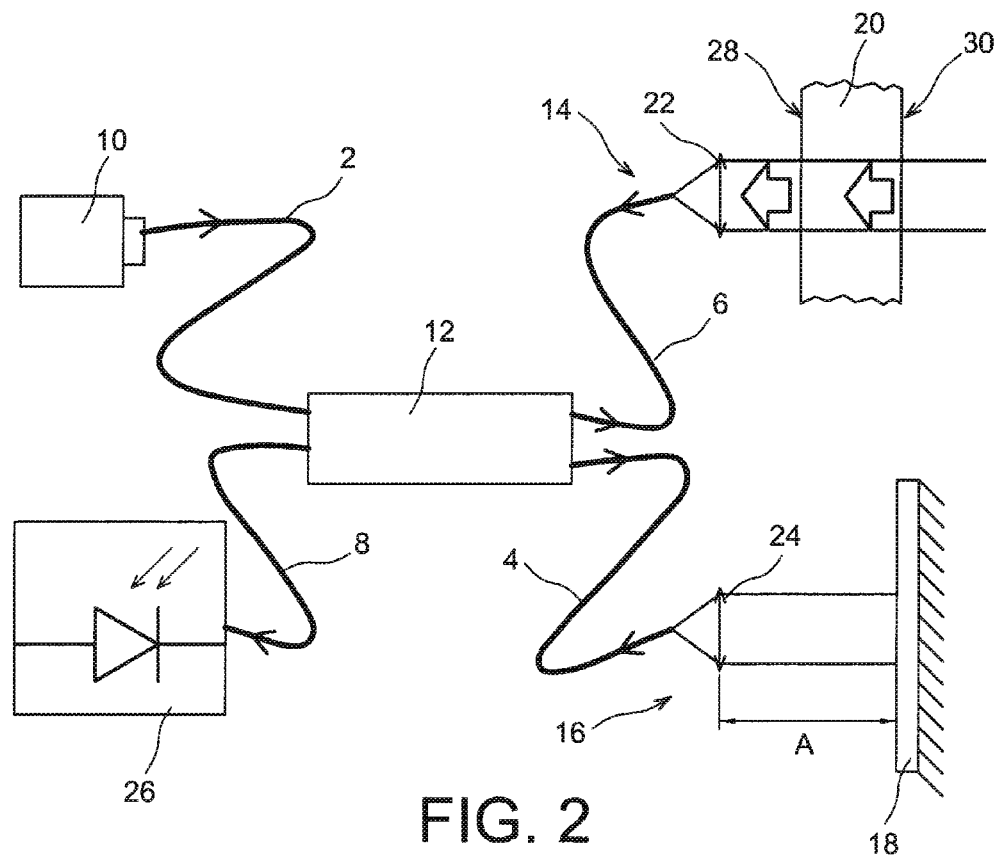
FIG. 2

METHOD FOR CONTACTLESS MEASUREMENT OF THE DENSITY OF A POROUS MATERIAL, USING A MEASUREMENT OF THE REFRACTIVE INDEX OF THE MATERIAL BY OPTICAL COHERENCE TOMOGRAPHY

CROSS REFERENCE TO RELATED APPLICATIONS or PRIORITY CLAIM

This application is a National Phase of PCT/EP2009/060021, filed Aug. 3, 2009, entitled, "CONTACTLESS METHOD OF MEASURING THE DENSITY OF A POROUS MATERIAL, USING A MEASUREMENT OF THE REFRACTIVE INDEX OF THE MATERIAL OBTAINED BY OPTICAL COHERENCE TOMOGRAPHY", and claims priority of French Patent Application No. 08 55426, filed Aug. 5, 2008.

TECHNICAL FIELD

The present invention relates to a method for contactless measurement of the density of a porous material.

This method uses contactless measurement of the refractive index of the material.

Let us from now on specify that the measurement of the refractive index of the material is carried out via a measurement of the thickness of a transparent or semi-transparent (i.e. translucent) layer, in a range of thicknesses from a few micrometres to several millimetres, and a measurement of the associated optical path.

The invention applies to planar layers as well as to layers of spherical or cylindrical shape and also to single-layer objects or to transparent multilayer stacks.

The originality of the method is based on the combination of an acquisition of signals obtained by optical coherence tomography, or OCT, which is a high resolution technique, and of measurements of thicknesses which are, for example, carried out by XR microradiography. With this combination, it is possible to accurately measure the refractive index of a material and to infer the local density therefrom in the case of porous materials or cellular materials or foams.

Thus, the invention allows contactless and non-destructive measurement of the density of a porous material. To do this, optical coherence tomography measurements and thickness measurements, for example by XR radiography, are combined, which in a first phase allows accurate measurement of the effective refractive index of the porous material in order to finally estimate the density of the material.

STATE OF THE PRIOR ART

The technique of optical coherence tomography (OCT) has been the subject of many scientific publications and its principle is used in the medical field (in particular in ophthalmology and in dermatology) for imaging transverse structures of biological tissues.

Only a few imaging techniques have revolutionized diagnostic medicine during the last decades: X-ray computed tomography or scannography, magnetic resonance imaging (MRI) and radio-isotope imaging. These techniques allow three-dimensional viewing; however, their spatial resolution is typically limited to a few millimetres in standard clinical practice.

Optical imaging techniques such as fluorescence or confocal microscopy allow axial and transverse resolutions of the order of one micrometre, but with limited penetration into biological tissues.

Ultrasonic examinations (or echographies), as for them, require physical contact with the object to be analyzed and provide an axial resolution of more than about hundred micrometres.

For about ten years, advances in optics in the field of optical fibres like in that of novel technologies of light sources, have allowed the development of a novel non-invasive and contactless optical medical imaging technique: optical coherence tomography. The two main features of this technique are the principle of interferometry on the one hand and the use of a source emitting a partly coherent light on the other hand.

In conventional interferometry, a source of light with strong coherence, of wavelength $\lambda$, is used for producing an interference over a large distance scale. OCT is a form of interferometry which uses a source of light with low coherence, in which case the interference only appears over very small distances. Thus, with the OCT technique, micrometric axial resolution may be obtained.

All this is schematized in FIGS. 1A and 1B where the changes in the intensity I of the interferometric signal versus the displacement $\Delta L$ of the reference mirror used for obtaining the interference are illustrated, in the case when a strongly coherent light source (see FIG. 1A) or a partly or weakly coherent source (see FIG. 1B, wherein $l_c$ represents the coherence length) is used.

Another technique called «interference spectrometry in white light» or «spectral interferometry in white light», allows measurement of the thickness of a transparent layer in a range of thicknesses from a few micrometers to several hundred micrometers. It applies to planar layers as well as to layers of spherical or cylindrical shapes and also to single-layer objects or transparent multilayer stacks. The measurement is conducted without any contact, with an accuracy attaining 100 nm.

However, this technique seems to be less adapted to the study of porous materials and to that of multilayer samples having small refractive index jumps.

DISCUSSION OF THE INVENTION

The object of the present invention is to find a remedy to the previous drawbacks.

With regard to existing applications, the method, object of the invention, has the following originalities:
 it relates to a range of thicknesses from less than 10 μm to several millimetres,
 it allows characterization of non-planar objects,
 it combines measurements of optical paths with measurements of thicknesses, for example by means of X-rays, for estimating the refractive index of bulk materials and the effective refractive index of porous materials, and
 it allows calculation of the local density of foams.

The invention mainly deals with a method allowing contactless and non-destructive measurement of the refractive index of deposits or hollow objects and of the density of the latter. This method uses the optical coherence tomography technique, combined with the measurement of thicknesses, for example by X-ray microradiography, or with the measurement of outer diameters (for spherical objects) preferably by backlit shadowgraphy.

The method has the following advantages:
 the measurement conducted by this method may be applied to a planar, cylindrical or spherical object, without using an illumination geometry adapted to the shape of the analyzed object,
 the measurement applies to single-layer or multilayer objects, the measurement is conducted without any contact and with working distances ranging from a few millimetres to several tens of centimetres, these distances depending on the collimator which may be used for implementing the method, the measurement may be conducted on objects, the thicknesses of which vary from a few micrometres to several millimetres, with the method it is possible to measure optical paths with an accuracy of about hundred nanometres, with the method it is possible to measure the refractive index of a bulk or porous sample, and with the method it is possible to measure the density of an object if it is porous.

The invention is mainly characterized by the use of the optical coherence tomography technique which will be described subsequently. The latter is combined with another instrumental technique in order to be able to determine the thicknesses, refractive indexes as well as the densities of the probed materials.

Optical coherence tomography is a technique which allows measurements of optical thicknesses to be carried out within the range of a few micrometres to several hundreds of millimetres according to the travel of the reference mirror used for its implementation (see above).

It allows contactless measurements and applies to transparent or translucent objects. It may be used on non-planar objects and on multilayer stacks. The measurements may be conducted by using low optical powers (about hundred μW) which ensure the non-destructive nature of the technique. Moreover with optical coherence tomography it is possible to obtain better resolutions than 1 μm (down to 100 nm).

The optical coherence tomography measurement method may be implemented at distances of several metres by using collimators. This remote measurement method may be useful for conducting measurements inside vacuum chambers of great dimensions by letting through the required light for implementing it through transparent windows or glove boxes.

Specifically, the object of the present invention is a contactless method for measurement of the density of a porous material, this material being characterized in that:

by a technique of optical coherence tomography, the optical path is determined corresponding to the crossing of an object made in the porous material by a light beam used for implementing the technique, the porous material being translucent or transparent to the light beam, the thickness of the object is determined, the refractive index of the porous material is determined, at the wavelength of the light beam, from the thereby determined optical path and thickness, and the density of the porous material is determined from the thereby determined refractive index.

Preferably, when the porous material consists of bulk material containing cells, the density $\rho_p$ of the porous material is determined by the following formula:

$$\rho_p = \rho_m \frac{n_p - 1}{n_m - 1}$$

wherein $n_p$ represents the refractive index of the porous material and $\rho_m$ and $n_m$ represent the density and the refractive index of the bulk (non-porous) material, respectively.

Preferably, the refractive index of the bulk material is determined by optical coherence tomography and by a thickness measurement from an object made with the bulk material.

The thickness of the object may be determined for example by X-ray radiography (preferably X-ray microradiography) or by optical backlit shadowgraphy.

According to a particular embodiment of the method of the invention, the object is spherical and hollow and thus has inner and outer diameters, and the inner diameter and the optical path or optical thickness (between two diametrically opposite points on the outer wall of the object), are determined by optical coherence tomography, and the outer diameter is determined by optical backlit shadowgraphy. By calculating half the difference between the thereby determined outer and inner diameters, it is possible to obtain the (geometrical) thickness of the object.

According to a particular embodiment of the invention, the object is spherical and hollow and thus has inner and outer diameters, and the object is attached to the end of a capillary thread in order to determine the optical path and the thickness of the object at a same point.

Indeed, the article of R. M. Almeida et al., « Sol-gel silica films on silicon substrates » , International Journal of Optoelectronics, Vol. 9, no. 2, March 1994, pp. 135-142, describes a method for measuring the refractive index of a porous material depending on the porosity percentage of this material. The measurement is conducted by ellipsometry and the results are estimated by verification with another method. But ellipsometry provides a value of the refractive index at the surface of the investigated sample. The estimation of the porosity is therefore also made at this level. With the method described in this document, the porosity in the thickness of the sample cannot be known.

On the contrary, the present invention uses the optical coherence tomography technique and, by the penetration power allowed by this technique, it is possible to measure the density and therefore the porosity in the thickness of the investigated porous material. Further, with the invention, it is possible to strictly calculate the density and not simply estimate the latter (one is capable of calculating a measurement uncertainty), by providing a law of the change in density versus the refractive index (and vice versa).

SHORT DESCRIPTION OF THE DRAWINGS

Figure 4A:
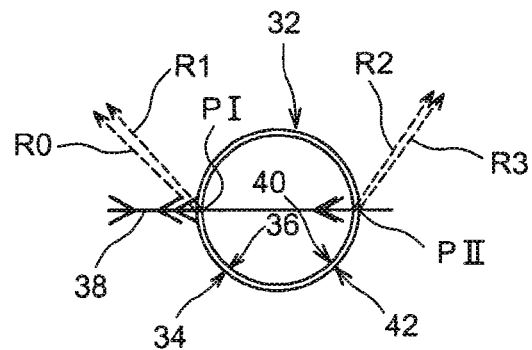
Figure 4B:
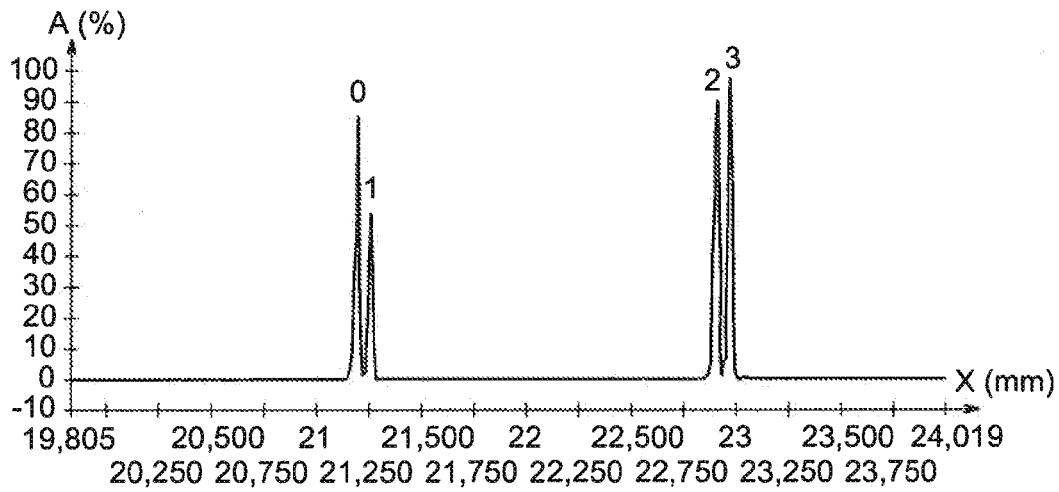
Figure 5:
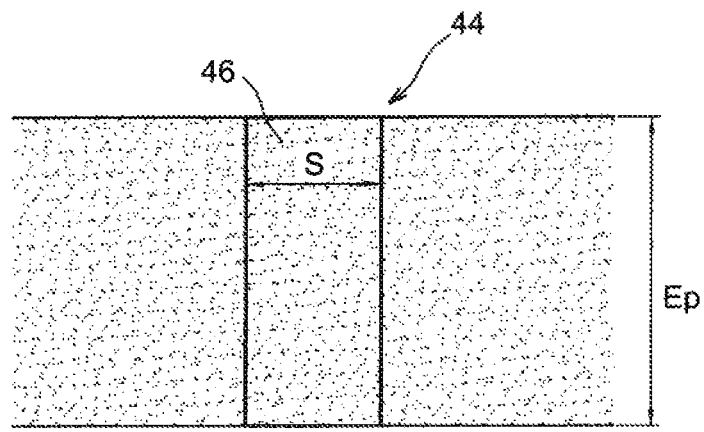
Figure 6:
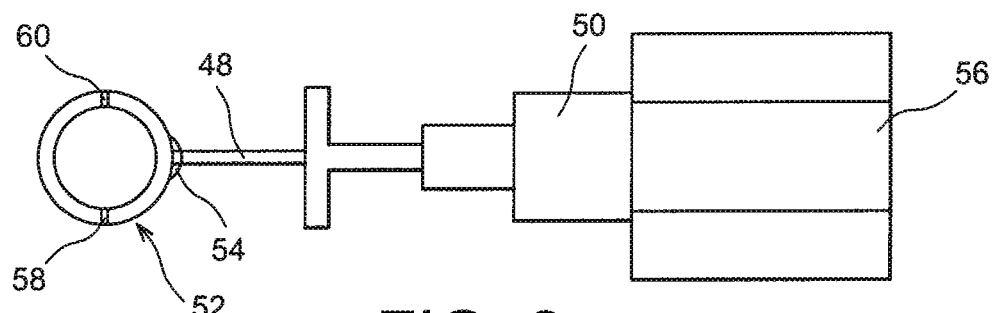
Figure 7:
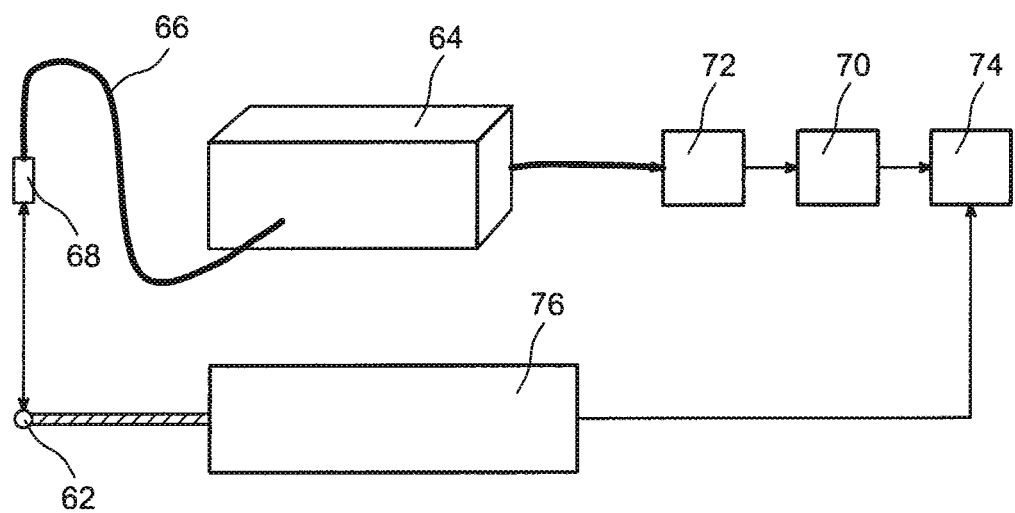

The present invention will be better understood upon reading the description of exemplary embodiments given hereafter purely as an indication and by no means as a limitation, with reference to the appended drawings, wherein:

FIGS. 1A and 1B, already described, show the variations of the intensity of an interferometric signal versus the displacement ΔL of a reference mirror used for obtaining interference, in the case when a strongly coherent light source (FIG. 1A) and a partly coherent light source (FIG. 1B) is used, FIG. 2 is a schematic view of an OCT system, which may be used for implementing the invention, FIG. 3 shows the OCT signature of a plastic microflask, FIG. 4A shows a single-layer microflask with a small thickness, FIG. 4B shows an OCT signal of the microflask of FIG. 4A, FIG. 5 shows a cellular polymer material or foam, FIG. 6 shows a microflask in foam, mounted on a capillary thread, and FIG. 7 is a schematic view of an OCT device for contactless measurement of optical paths.

DETAILED DISCUSSION OF PARTICULAR EMBODIMENTS

First, let us refer back to the optical coherence tomography measurement.

Considerably widespread in medicine, biology and industry, optical coherence tomography or OCT which is used in the present invention, is based on the principle of Michelson interferometers. FIG. 2 is a schematic view of OCT system which may be used for implementing the invention. This system includes a Michelson interferometer with optical fibres. The optical fibres have references 2, 4, 6, 8 in the figure. The system also comprises a partly coherent light source 10, formed by a superluminescent diode or SLD in the example, the emission of which is centred in the near infrared with a full spectral width at half maximum, or FWHM, of a few tens of nanometres.

The light wave emitted by the source 10 is divided by means of a coupler 12 between the measurement arm 14 and the reference arm 16 of the system.

In the reference arm, which forms an optical delay line, light is reflected by a mirror 18 which is mounted on a translation system (not shown) including an incremental optical encoder for accurately controlling its position. The mirror moves over a range of a few millimetres to several hundred millimetres, corresponding to the maximum probed depth of the measured sample 20. The acquisition time is less than one second for travels of the order of one millimetre.

In the measurement arm 14, the light wave is injected into the optical fibre 6 which is a low dispersion single-mode fibre.

The measurement arm 14 and the reference arm 16 respectively include collimators 22 and 24. The distance of the mirror 18 to the collimator 24 is noted as A.

The light waves reflected by the reference mirror 18 and by one of the interfaces 28 and 30 of the sample 20 are recombined on the detector 26 of the system, a photodiode in the example (which is connected to signal processing means not shown), and produce an interference signal when the optical paths in the two arms of the interferometer are equal, to within the coherence length $l_c$.

This coherence length $l_c$ is set by the characteristics of the wave emitted by the source 10. It is possible to write:

$$l_c = \frac{2 \cdot \ln 2}{\pi} \cdot \frac{\lambda_c^2}{\Delta \lambda}$$

wherein $\lambda_c$ corresponds to the central wavelength of the light emission and $\Delta\lambda$ to the full spectral width at half maximum (FWHM).

Purely as an indication and by no means as a limitation, a system is used in which $\lambda_c$ has the value of 1,310 nm and $\Delta\lambda$ has the value of 60 nm, so that $l_c$ is equal to 12.6 µm.

With such a coherence length of 12.6 µm, it is not possible to «see» (and to measure with the OCT technique) layers for which the optical thickness (geometrical thickness×optical index) is less than 12.6 µm. For materials for which the optical index is of the order of 1.5, this limit corresponds to (geometrical) thicknesses of 8 µm. Nevertheless, it is possible to decrease the coherence length $l_c$ down to a value of 5 µm with present technologies of SLD sources with a wide emission band (larger $\Delta\lambda$), and even down to a value of the order of 1 µm by using a femtosecond solid laser source as a source 10.

The interference signal $I(\delta L)$ of the OCT system is proportional to:

$$1 + R + 2 \cdot \sqrt{R} \cdot \exp\left(-4 \cdot \ln 2 \cdot \frac{\delta L^2}{l_c^2}\right) \cdot \cos\left(\frac{4 \cdot \pi}{\lambda_c} \cdot \delta L\right)$$

wherein $\delta L$ is the optical path difference between both arms of the interferometer and R is the reflection coefficient of the interface of the sample 20. This is expressed by a signal including one peak per interface encountered by the light. The position of the maximum of this peak corresponds to the position of the interface. The separation between two consecutive peaks is connected to the optical distance covered by the light wave between both associated interfaces. By knowing the refractive index of the medium comprised between both of these interfaces, it is easy to calculate the thickness of the probed medium.

As an example, FIG. 3 shows the OCT signature (amplitude A versus position X) of a microflask in plastic material, the outer diameter and the thickness of which have the values of 2.23 mm and 166 µm, respectively. Four peaks are seen which are noted as 0, 1, 2, 3 and correspond to the four interfaces encountered by the light in the case of this microflask.

The accuracy on the measurement of the differences in optical paths, associated with the accurate measurement of the position of the reference mirror, is less than 300 nm (a datum from the manufacturer of the system, related to the technology of the tables used and to the method for detecting the peaks).

An OCT signal therefore has a succession of peaks, each of them corresponding to the reflection of the light beam on an interface of the measured sample. Each peak is accurately defined by its position on the path of the beam. It is therefore possible to deduce the optical path corresponding to a difference of two positions which separate two interfaces of the sample. This optical path is directly proportional to the thickness of the material comprised between these two interfaces, multiplied by the refractive index of the material for the central wavelength $\lambda_c$ of the source.

By combination with a method for measuring thicknesses, the OCT measurements of the differences in optical paths give the possibility of estimating the refractive index of the material of the measured sample, a microflask in the example of FIG. 3.

From the average thickness values, obtained for example by XR microradiography, and by knowing by OCT the optical paths corresponding to the crossing of these thicknesses, it is possible to estimate the refractive index of each investigated microflask.

The formula linking the thickness Ep of a material of refractive index n to the optical path L corresponding to the crossing of this material by light is:

$$L = n \times Ep \text{ hence } n = \frac{L}{Ep}$$

The uncertainty $\Delta n$ associated with the measurement of n is written as:

$$\Delta n = \frac{\Delta L \cdot Ep + L \cdot \Delta Ep}{Ep^2}$$

The measurement of the refractive index of a porous material, such as a cellular material or a foam, gives the possibility of contemplating characterization of the local density at the measurement point of the material. Indeed, for an object (such a microflask) which is not very dense, the refractive index will be close to 1, the value of the refractive index of air. Further by knowing the index of the bulk material, it is possible to estimate the proportion of probed material on a pole of the microflask, with respect to the amount of air which has been crossed, and therefore to calculate the density of the microflask at this pole.

OCT optical and XR microradiography characterizations were carried out on a microflask 32 (FIG. 4A) formed by a single layer of plastic material (CH polymer). This microflask is synthesized by plasma deposition (GDP); its outer diameter is of the order of 2 mm and its thickness of the order of a few tens of micrometres.

FIG. 4B shows the OCT signal corresponding to the average of 20 acquisitions for this microflask, over a probing depth of 40 mm. The signal includes four peaks which are noted as 0, 1, 2, 3. The pair of left peaks 0-1 corresponds to the R0-R1 reflections (FIG. 4A) on the outer and inner interfaces 34-36 of the first wall encountered by the measurement light beam 38, at a first pole PI. The pair of right peaks 2-3 corresponds to the reflections R2-R3 on the outer and inner interfaces 40-42 of the second wall of the microflask at a second pole PII.

The results obtained for the measurements of optical thicknesses at both poles and for the internal diameter of the microflask are given in Table I.

TABLE I

|  | $1^{st}$ pole | Inner diameter | $2^{nd}$ pole |
|---|---|---|---|
| Optical paths L (μm) | 61.9 | 1646.3 | 61.1 |

The same microflask was microradiographed with X radiation. The exposure parameters under the microradiography column are:
exposure time: 45 minutes,
chromium tube,
voltage: 15 kV,
intensity: 20 mA.

The developed radiographic plate is then digitized with an optical digitization system, comprising a Nikon microscope with ×20 magnification, equipped with a high resolution CCD camera. With the components of this digitization system, about eight images are required for covering the whole of the perimeter of a microflask.

Next, with suitable software, a radial intensity profile is extracted from each image and allows manual measurement of a thickness by positioning cursors on the profile. An average on the equator (8 snapshots and profiles) provides the thickness of the microflask.

However it is specified that the thickness of the microflask may be measured by techniques other than X radiography, for example by optical backlit shadowgraphy or by means of a mechanical feeler.

For this microflask, already characterized by OCT, the average thickness measured by X radiation has the value:

$Ep=(39.8\pm0.9)$ μm

Thus it is possible to estimate the refractive index of the constitutive plastic material of the microflask. At 1,310 nm this index has the value:

$n=1.55\pm0.04$

The uncertainty of 0.04 on the refractive index is essentially due to the uncertainty on the thickness measurement by X radiation (0.9 μm) and to the fact that the a layer of rather small thickness was characterized.

It is also possible to calculate the refractive index of spherical samples with two optical techniques, by carrying out the combination of OCT with a measurement of the outer diameter of the microflask by single-view backlit shadowgraphy, more simply, called backlit shadowgraphy. Indeed, the difference between this outer diameter $\phi_{ext}$ (measured by means of the telecentric objective of backlit shadowgraphy) and the inner diameter $\phi_{int}$ obtained by means of OCT makes it possible to estimate the thickness $$Ep = \frac{1}{2}(\varphi_{ext} - \varphi_{int})$$

of the walls of the sample; and, as earlier, the ratio between the optical path L (also obtained by OCT) and the thickness Ep gives the refractive index n(=L/Ep) of the material with which the microflask is made up.

On the subject of backlit shadowgraphy, reference will notably be made to the following documents:

[1] International Application WO 2004/083772 A published on Sep. 30, 2004 « Method for measurement of three-dimensional objects by single-view backlit shadowgraphy»

[2] International Application WO 2006/030149 A published on Mar. 23, 2006, « Method for measuring three-dimensional objects by a single-view backlit shadowgraphy using optical laws of light propagation»

[3] International Application WO 2008/023024 A published on Feb. 28, 2008, « Method for the contactless measurement of two-layered three-dimensional objects by single-view backlit shadowgraphy»

The combination of optical measurements mentioned above seems to be very powerful and more comfortable than the combination of OCT and X-ray radiography, notably because a backlit shadowgraphy system is less bulky than an X-radiation characterization system.

Just as the refractive index of a microflask in bulk material (see above) may be estimated, similarly the refractive index of a porous material may be estimated: the association of the two characterization techniques may also be applied to the thickness measurement of microflasks made in cellular polymer or foam material. In the same way as previously, the measurements make it possible to estimate the effective refractive index for a sample, which consists of gas-containing cells which are trapped in a bulk polymer.

From the value of the effective refractive index and by knowing the refractive index of the bulk polymer and the density of the latter, the local density of the foam, i.e. its density at the location of the measurement may be estimated.

The investigated foam microflasks have an outer diameter of about 2 mm, a thickness of about 100 μm, a density from 50 to 250 mg/cm² as well as sphericity and concentricity of more than 99%.

FIG. 5 shows a layer 44, of thickness Ep, of polymeric cellular material or polymeric foam for which the effective refractive index $n_M$ is known. The values of the refractive index of the bulk polymer $n_{CHx}$ at the same investigation wavelength and of the density of this bulk polymer $\rho_{CHx}$ are also known.

In a portion 46 of volume $V_T$ of the layer 44, the density $\rho_m$ of the material is the ratio between the total mass $m_T$ of the portion and the volume $V_T$ occupied by this portion:

$$\rho_M = \frac{m_T}{V_T}$$

The respective masses $m_{CHx}$ and $m_A$ of both elements making up the volume occupied by the foam, i.e. the bulk polymer and the air contained in the cells, verify the relationship:

$$m_T = m_{CHx} + m_A$$

It is also possible to write:

$$m_T = \rho_{CHx} \cdot V_{CHx} + \rho_A \cdot V_A \text{ and } V_T = V_{CHx} + V_A$$

wherein $\rho_{CHx}$ and $\rho_A$ are the densities of the bulk polymer and of air respectively, and $V_{CHx}$ and $V_A$ are the respective volumes of the bulk polymer and of air, the sum of which corresponds to $V_T$.

Thus, the density of the foam is written as:

$$\rho_M = \frac{\rho_{CHx} \cdot V_{CHx} + \rho_A \cdot V_A}{V_{CHx} + V_A}$$

We consider here that the volume of each probed material (bulk CHx or air) corresponds to the product of the section S of the foam portion, probed by the light beam, by the associated material thickness, noted as $l_{CHx}$ for the bulk $CH_x$ and $l_A$ for air. Hence:

$$V_{CHx} = S \cdot l_{CHx} \text{ and } V_A = S \cdot l_A \quad (1)$$

$$\rho_M = \frac{\rho_{CHx} \cdot l_{CHx} + \rho_A \cdot l_A}{l_{CHx} + l_A} = \frac{\rho_{CHx} \cdot l_{CHx} + \rho_A \cdot l_A}{Ep}$$

We shall now express each thickness $l_{CHx}$ and $l_A$ as a function of the refractive indexes of the foam $n_{CHx}$ of the bulk polymer $n_{CHx}$ and of air $n_A$.

We may first express the total thickness Ep of the foam as a function of the "partial" thicknesses $l_{CHx}$ and $l_A$ and as a function of the total optical path D and of the "partial" optical paths $d_{CHx}$ and $d_A$:

$$Ep = l_{CHx} + l_A$$

and $$Ep = \frac{D}{n_M} = \frac{d_{CHx} + d_A}{n_M} = \frac{1}{n_M} \cdot (n_{CHx} \cdot l_{CHx} + n_A \cdot l_A)$$

Both of these latter equations allow the thicknesses $l_{CHx}$ and $l_A$ to be expressed as a function of the refractive indexes:

$$l_{CHx} = \frac{n_M - n_A}{n_{CHx} - n_A} \cdot Ep$$

$$l_A = \frac{n_{CHx} - n_M}{n_{CHx} - n_A} \cdot Ep$$

By carrying over these values into equation (1), one obtains:

$$\rho_M = \frac{n_M - n_A}{n_{CHx} - n_A} \cdot \rho_{CHx} + \frac{n_{CHx} - n_M}{n_{CHx} - n_A} \cdot \rho_A \quad (2)$$

$$\rho_M = \frac{\rho_A \cdot n_{CHx} - \rho_{CHx} \cdot n_A}{n_{CHx} - n_A} + \frac{\rho_{CHx} - \rho_A}{n_{CHx} - n_A} \cdot n_M$$

By considering the density of air as negligible compared with that of the bulk polymer ($\rho_A$ of the order of $10^{-3} \rho_{CHx}$) and by giving the value 1 to the air refractive index, equation (2) becomes:

$$\rho_M = \rho_{CHx} \cdot \frac{n_M - 1}{n_{CHx} - 1} \quad (3)$$

Equation (3) allows determination of the density of the polymer foam by a simple measurement of its effective refractive index, provided that the values of the density and of the refractive index are known of the bulk material from which the foam is formed, i.e. the bulk polymer.

Localized measurements of thickness, by X-ray microradiography, and of the associated optical path, by OCT, allow determination of the effective refractive index of the foam sample (this is also applicable to the bulk polymer) and therefore determination of its local density.

Now an example of an estimation of the local density of a foam microflask is given.

A microflask in polymer foam CHx is considered, the synthesis of which has allowed the following parameters to be targeted:

an outer diameter of 2 mm,
a thickness of 100 μm, and
a density of 250 mg/cm³.

This microflask was mounted on an assembly which allows XR and OCT characterizations in a same location of the foam. This assembly is schematically illustrated in FIG. 6 and comprises a capillary thread 48 and a capillary support 50 allowing a measurement by X-ray radiography. The microflask 52 is attached to an end of the capillary thread 48 by an adhesive spot 54. The other end of the capillary thread is attached to the support 50.

In a first phase, a measurement of the refractive index of the bulk polymer CHx was conducted on a sample of CHx formed by polymerization under ultraviolet radiation. This sample was machined in order to make it more homogeneous along its thickness. The sample of bulk CHx then appears as a disk with a diameter of 11 mm and a thickness of about 2 mm.

This disk of bulk CHx was characterized by means of a contact feeler system (touching tip) and by means of OCT in order to obtain the thickness and the associated optical path, respectively. From these results, the refractive index of the sample may be estimated at a wavelength of 1,310 nm which is the OCT working wavelength.

From these measurements, it was inferred that the refractive index of the bulk polymer CHx had the value:

$$n_{CHx} = 1.511 \pm 0.001 \text{ at } 1{,}310 \text{ nm}$$

By means of a flat 56 present on the support 50 of the capillary thread, the CHx foam microflask was characterized in thickness by X-ray microradiography in two specific areas 58 and 60 of the microflask. As this is seen, both areas are diametrically opposite and delimit a diameter which is perpendicular to the capillary thread. It is proceeded with one measurement, by OCT, of the optical path corresponding to the crossing of both of these same areas 58 and 60.

The different results obtained allow determination of the effective refractive index $n_M$ of the foam of CHx at 1,310 nm:

| | |
|---|---|
| average thickness | 101.9 μm |
| average optical path | 113.9 μm |
| refractive index $n_M$ | 1.117 |

Thus, one has the value of the refractive index of the bulk polymer and its density and now the refractive index of the foam sample is known:

$\rho_{CHx} = 1,188 \text{ kg/m}^3$ $n_{CHx} = 1.511 \text{ at } 1,310 \text{ nm}$ $n_M = 1.117 \text{ at } 1,310 \text{ nm}$ By carrying over these numerical data into equation (3), it is possible to calculate the density of the polymer foam CHx. For the relevant sample, the density has the value of:

$\rho_{CHx} = 272 \text{ kg/m}^3 \text{ (or mg/cm}^3\text{)}$

By determining the weight on microscales, the mass $m_{\mu b}$ of the microflask is obtained:

$m_{\mu b} = 317 \text{ µg} \pm 1 \text{ µg}$

By a measurement of the outer diameter $\phi_{ext}$ with a telecentric objective by backlit shadowgraphy, associated with the thickness measurement by X-ray radiography, it is possible to calculate the volume $V_{\mu b}$ of the material forming the microflask. One obtains:

$\phi_{ext} = 2,027 \text{ µm} \pm 1 \text{ µm and } Ep = 101.4 \text{ µm} \pm 0.9 \text{ µm}$ These measurements give an average value of the density of the CHx polymer foam:

$$\rho'_{CHx} = \frac{m_{\mu b}}{V_{\mu b}}$$

with $$V_{\mu b} = \frac{4 \cdot \pi}{3} \cdot \left[ \left(\frac{\phi_{ext}}{2}\right)^3 - \left(\frac{\phi_{ext}}{2} - Ep\right)^3 \right]$$

The numerical value of the overall density of the microflask (a value to be compared with the one which was found above) is:

$\rho CHx' = 267 \text{ mg/cm}^3 \pm 6 \text{ mg/cm}^3$

A local density measurement at a point of the microflask may be different from the overall density measurement; the local density measurement, determined from the refractive index of the foam, is nevertheless included in the uncertainty range of the calculated overall density.

FIG. 7 is a schematic view of an optical coherence tomography device for contactless measurement of optical paths. The light source used for illuminating the object to be characterized 62 is a superluminescent diode which emits in the infrared. This source, the reference arm of the interferometer and the analysis electronics are integrated into a casing 64; only one optical fibre 66 exits from the casing, forming a portion of the measurement arm of the interferometer 64.

This optical fibre ends with a collimator which is used for illuminating the object to be analyzed and for collecting the reflected light. Its nature allows the working distance to be adapted between the outlet of the fibre and the object to be characterized, from a few millimetres to several tens of centimetres.

The analyzed interferometric signal is transmitted up to a computer 70 via an acquisition card 72 provided for obtaining the optical paths which characterize the investigated object. The computer 70 is provided with means 74 for displaying the obtained results.

The complementary characterization means 76 (X-ray microradiography system for the thickness or backlit shadowradiography system for the outer diameter) allows the effective refractive index of the object and the density of the latter to be calculated in the case when this is a porous sample. The results obtained by this complementary characterization means are also utilized by the computer 70.

Optical coherence tomography may be used for the contactless and non-destructive measurement of optical paths of polymeric films such as those which are used in the packaging industry. Its combination with a thickness measurement allows determination of the refractive index of a sample as well as of the density of this sample in the case when it is made from a porous material, in particular a porous heat insulator material.

The OCT technique may also be used for characterizing coatings deposited on another material, in particular during inspections on manufacturing lines. Indeed, with this technique it is possible to differentiate the particular optical paths of a multilayer sample.

The optical coherence tomography technique was used for characterizing hollow flasks with a diameter of 2 mm, made from polymers of different natures. Measurements were also conducted on flasks for which the thicknesses varied between 10 µm and 180 µm. These results show the wide field of applications of the technique in terms of measurement of refractive index.

The technique may also be applied to the measurement of the thickness of a layer of translucent or transparent material, which has been deposited inside a flask made from a polymer. This for example may be a layer of hydrogen isotopes which have been solidified at a cryogenic temperature.

Further, the optical coherence tomography technique was used on spherical and hollow objects in polymeric foam, with an external diameter of 2 mm and a thickness of about 100 µm. Their effective refractive index was able to be calculated. By a measurement of the refractive index of the bulk polymer, it was possible to calculate the local density of the polymer foam.

The invention claimed is:

1. A method for contactless measurement of a density of a porous material, the method comprising:
    determining an optical path corresponding to a crossing of an object, made of the porous material, by an optical coherence tomography technique using a light beam, the porous material being translucent or transparent to the light beam,
    determining a thickness of the object,
    determining a refractive index of the porous material, at a central wavelength of the light beam, from the determined optical path and thickness, and
    determining the density of the porous material from the determined refractive index, wherein the object is spherical and hollow and has outer and inner diameters, the inner diameter and the optical path are determined by optical coherence tomography, the outer diameter is determined by backlit shadowgraphy, and the thickness of the object is determined by calculating half the difference between the determined outer and inner diameters.

2. The method according to claim 1, wherein the porous material consists of a bulk material containing cells and the density $\rho_p$ of the porous material is determined by the following formula:

$$\rho_p = \rho_m \frac{n_p - 1}{n_m - 1}$$

wherein $n_p$ represents the refractive index of the porous material and $\rho_m$ and $n_m$ respectively represent the density and the refractive index of the bulk material.

3. The method according to claim 2, wherein the refractive index of the bulk material is determined by optical coherence tomography and by a thickness measurement from an object made from the bulk material.

\* \* \* \* \*

UNITED STATES PATENT AND TRADEMARK OFFICE
CERTIFICATE OF CORRECTION

PATENT NO. : 8,488,112 B2
APPLICATION NO. : 13/057153
DATED : July 16, 2013
INVENTOR(S) : Jeannot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Eighth Day of September, 2015

Michelle K. Lee
*Director of the United States Patent and Trademark Office*